US008642289B2

(12) United States Patent
Sant'Anna et al.

(10) Patent No.: US 8,642,289 B2

(45) Date of Patent: Feb. 4, 2014

(54) PROCESS FOR PRODUCING ETHANOL FROM A HYDROLYSATE OF THE HEMICELLULOSE FRACTION OF SUGARCANE BAGASSE IN A PRESS REACTOR

(75) Inventors: Lidia Maria Melo Sant'Anna, Niteroi (BR); Nei Pereira, Rio de Janeiro (BR); Gabriel Jaime Vargas Bitancur, Rio de Janeiro (BR); Juliana Vaz Bevilaqua, Rio de Janeiro (BR); Absai da Conceicao Gomes, Rio de Janeiro (BR); Emerson Pires Menezes, Rio de Janeiro (BR)

(73) Assignee: Petroleo Brasileiro S.A.—Petrobras, Rio de Janeiro (BR)

( * ) Notice: Subject to any disclaimer, the term of this patent is extended or adjusted under 35 U.S.C. 154(b) by 544 days.

(21) Appl. No.: 12/667,369

(22) PCT Filed: Jul. 3, 2007

(86) PCT No.: PCT/GB2007/002468

§ 371 (c)(1), (2), (4) Date: Jul. 13, 2010

(87) PCT Pub. No.: WO2009/004273

PCT Pub. Date: Jan. 8, 2009

(65) Prior Publication Data

US 2010/0273228 A1 Oct. 28, 2010

(51) Int. Cl.
*C12P 1/00* (2006.01)

(52) U.S. Cl.
USPC .............................. 435/41; 435/161; 435/171

(58) Field of Classification Search
USPC ........................................... 435/41, 161, 171
See application file for complete search history.

(56) References Cited

U.S. PATENT DOCUMENTS

2002/0164730 A1* 11/2002 Ballesteros Perdices et al. ............................ 435/163

FOREIGN PATENT DOCUMENTS

| | | | |
|---|---|---|---|
| WO | 01/32715 | A1 | 5/2001 |
| WO | 2004/049818 | A1 | 6/2004 |
| WO | 2006/086861 | A2 | 8/2006 |

OTHER PUBLICATIONS

Rodrigues et al. "The influence of pH, temperature and hydrolyzate concentration on the removal of volatile and nonvolatile compounds from sugarcane bagasse hemicellulosic hydrolyzate treated with activated charcoal before or after vacuum evaporation", Braz. J. Chem. Eng., 2001, 18(3):1-21.*

Ferrari, M.D., et al, "Ethanol Production From Eucalyptus Wood Hemicellulose Hydrolysate by *Pichia stipitus*", Biotechnology and Bioengineering, 1992, pp. 753-759, vol. 40, Issue 7.

Moniruzzaman, M., "Alcohol Fermentation of Enzymatic Hydrolysate of Exploded Rice Straw by *Pichia stipitis*", World Journal of Microbiology & Biotechnology, 1995, pp. 646-648, vol. 11.

Gurgel, P.V., et al., "Evaluation of Sugarcane Bagasse Acid Hydrolyzate Treatments for Xylitol Production", Brazilian Journal of Chemical Engineering, Sep. 1998, vol. 15, No, 3.

Nigam, J.N., "Ethanol Production From Hardwood Spent Sulfite Liquor Using An Adapted Strain Of *Pichia stipitis*", Journal of Industrial Microbiology and Biotechnology, Mar. 2001, pp. 145-150, vol. 26 (3).

Castro Heather F. De, et al., "Alternative Approach for Utilization of Pentose Stream From Sugarcane Bagasse by an Induced Flocculent *Pichia stipitis*", Applied Biochemistry and Biotechnology. Apr. 2003, pp. 547-556. vol. 107, Nos. 1-3.

Jeffres, T. W., et al, "Genetic Engineering of *Pichia stipitus* For The Improved Fermentation of Xylose", BioEnergy Jun. 1998, Expanding BioEnergy Partnerships, pp. 643-851: 7$^{th}$ International Conference on Biotechnology in the Pulp and Paper Industry—Vancouver, BC, Canada, Jun. 16-19, 1998.

Roberto, I.C., et al., "Utilization of Sugar Cane Bagasse Hemicellulosic Hydrolysate by *Pichia stipitis* for the Production of Ethanol", Process Biochemistry. 1991, pp. 15-21, vol. 26.

Van Zyl, C., et al., "Production of Ethanol from Sugar Cane Bagasse Hemicellulose Hydrolyzate by *Pichia stipitis*", Applied Biochemistry and Biotechnology, 1988, pp. 357-369, vol. 17.

Amartey, S., et al., "An Improvement in *Pichia stipitis* Fermentation of Acid-Hydrolysed Hemicellulose Achieved by Overtiming (Calcium Hydroxide Treatment) and Strain Adaptation", World Journal of Microbiology and Biotechnology, 1996, pp. 281-283, vol. 12, No. 3.

Database WPI Week 200779, Thomson Scientific. London, GB; 2007-846583 XP002469578 & BR PIO 505 299 A (Petrobras Petroleo Brasil S. A.) Aug. 7, 2007.

* cited by examiner

*Primary Examiner* — Bin Shen

(74) *Attorney, Agent, or Firm* — Sughrue Mion, PLLC

(57) ABSTRACT

The invention is a process for producing ethanol from sugarcane bagasse, the principal steps of which are mild sulphuric acid hydrolysis of the hemicellulose fraction of the sugarcane bagasse, followed by extraction of the hydrolysate and then fermentation thereof with the yeast *Pichia stipitis*. The process can be carried out with different solid : liquid ratios, and provides a step of acclimatizing the *Pichia stipitis* yeast, which results in a greater rate of ethanol production. The process takes place in a press reactor specially designed for this purpose, which allows more efficient extraction of the hydrolysate and, as a consequence, better process performance.

9 Claims, No Drawings

PROCESS FOR PRODUCING ETHANOL FROM A HYDROLYSATE OF THE HEMICELLULOSE FRACTION OF SUGARCANE BAGASSE IN A PRESS REACTOR

CROSS REFERENCE TO RELATED APPLICATION

This application is a National Stage of International Application No. PCT/GB2007/002468 filed Jul. 3, 2007.

FIELD OF THE INVENTION

The present invention is a fermentation process for producing ethanol using as starting material sugarcane bagasse, and more specifically a hydrolysate of the hemicellulose fraction of sugarcane bagasse, obtained by mild hydrolysis of sugarcane bagasse with sulphuric acid. The hydrolysed material is pressed from the solid matter while still within the reactor and the hydrolysate is neutralized with calcium hydroxide, so as to favour the fermentation process using a strain of the yeast *Pichia stipitis* duly adapted and acclimatized to the principal substrate of the hydrolysate.

BACKGROUND OF THE INVENTION

Brazil is one of the world's main producers of ethanol from sugarcane, generating substantial residues in the form of sugarcane bagasse. This enormous quantity of bagasse has considerable potential for use as starting material for the production of ethanol by biotechnological processes.

Currently, a large proportion of the bagasse produced in the country is burned to produce energy within the ethanol production plants themselves. However, there is considerable excess (of the order of 16 million tonnes) which could cause serious environmental problems.

PRIOR ART

Therefore, technology for producing ethanol from this excess bagasse, in addition to contributing towards solving environmental problems would also add value to this agroindustrial waste product, resulting in economic advantages for the country.

The development of biotechnology has resulted in new techniques for manipulating microorganisms so as to make them more resistant and capable of adapting to more adverse environments. Thus, many studies have been directed towards making use of industrial by-products or agricultural residues, and especially of cellulose-based materials such as cereal straw, maize cobs, chips of different types of woods, and sugarcane bagasse, etc., and also techniques for adapting microorganisms exclusively for industrial scale production of alcohol.

Published studies by M. D. Ferrari et al., "Ethanol production from eucalyptus wood hemicellulose hydrolysate by *Pichia stipitis*" (John Wiley & Sons, Inc. 1992), M. Moniruzzaman, "Alcohol fermentation of enzymatic hydrolysate of exploded rice straw by *Pichia stipitis*" (World Journal of Microbiology & Biotechnology 11: 646-648, 1995); P. V. Gurgel et al., "Evaluation of sugarcane bagasse acid hydrolyzate treatments for xylitol production", (Braz. J. Chem. Eng., Vol. 15, No. 3, São Paulo Sept. 1998), J. N. Nigam, "Ethanol production from hardwood spent sulfite liquor using an adapted strain of *Pichia stipitis*" (Journal of Industrial Microbiology & Biotechnology 26: 145-150. 2001), and Heizir F. de Castro et al., "Alternative approach for utilization of pentose stream from sugarcane bagasse by an induced flocculent *Pichia stipitis*" (Applied Biochemistry and Biotechnology, Vol. 107, No. 1, 3 Apr. 2003, pp 547-556 (10)), are evidence of the efforts of specialists worldwide to achieve their objectives. However, although the results have been promising, they are still unsatisfactory, because the yields achieved are less than those desired.

The process for producing alcohol according to the present invention represents an important advance as regards achieving Brazilian targets, by giving results which have not been obtained hitherto.

According to T. W. Jeffries—"Genetic Engineering of *Pichia stipitis* for the improved fermentation of xylose" (7th International Conference on Biotechnology in the Pulp and Paper Industry, Vancouver, BC, Canada, 16-19 Jun. 1998), the yield normally achieved in these processes is 0.3 to 0.44 g ethanol/g substrate such as xylose, and the rate of production is around 0.5 g/L.h.

With the process of the present invention it has been possible to achieve production rates of up to 1.10 g/L.h. This is an increase in the rate of production of the order of 120% compared with the prior art, making the process economically viable on an industrial scale; and it solves the environmental problems resulting from excess cane residues.

These and other advantages will become clear as the invention is described in more detail.

SUMMARY OF THE INVENTION

In the process for producing ethanol from sugarcane bagasse according to the present invention, the principal steps are mild sulphuric acid hydrolysis of the hemicellulose fraction of the sugarcane bagasse, followed by extraction of the hydrolysate and then fermentation with the yeast *Pichia stipitis*. The process can be carried out with different solid:liquid ratios, and more especially in the proportions 1:4 or 1:2 (g dry bagasse:mL acid solution).

The process takes place in a press reactor specially designed for this purpose, which allows more efficient extraction of the hydrolysate, and consequently better process performance.

It also includes acclimatization of the *Pichia stipitis* yeast, thereby increasing the yield and production rate of the process.

DETAILED DESCRIPTION OF THE INVENTION

The first step in the process comprises mild hydrolysis of sugarcane with 1% sulphuric acid, with the objective of preferential production of pentoses and especially xyloses, which are the principal components of hemicellulose. It is known that more violent hydrolysis of the cellulose fibres of bagasse results in the formation of products such as furfural, heavy metals, terpenes, tannins, phenol compounds, etc., which inhibit the growth of the yeast.

Initially, the *Pichia stipitis* is acclimatized and adapted to the fermentation environment by using the technique of sequential cell culture in culture media with gradually increasing contents of hydrolysate.

Broadly speaking, the basic steps of the process are as follows:

a) homogenization of the sugarcane bagasse together with dilute (1%) sulphuric acid in the selected solid:liquid ratio;
b) hydrolysis of the homogenized material in a special press reactor (described below), using an autoclave with a pressure of 1 atm (corresponding to a temperature of 121° C.)

for a duration that is decided to suit the solid:liquid ratio, but preferably in the range from 30 to 50 minutes;

c) extraction of the liquid phase (hydrolysate), inside the press reactor;

d) neutralization of the hydrolysate using calcium hydroxide;

e) filtration of the hydrolysate;

f) fermentation of the hydrolysate using an initial concentration of acclimatized *Pichia stipitis* biomass, or supplemented with the same, with stirring and aeration.

Runs were carried out using solid:liquid ratios of 1:4 and 1:2 for hydrolysis, and fermentation was performed at 3° C., with stifling at 500 rpm and an aeration rate 0.02 and 0.05vvm depending on the selected solid:liquid ratio, for about 24 to 40 hours in a BIOSTAT E® bioreactor. In the runs using lower solid:liquid ratios, the hydrolysate was supplemented by concentrating the acclimatized biomass.

The average results are presented in Table 1 below.

TABLE 1

| A (g:mL) | B (g/L) | C (g/L) | D (g/g) | E (g/g) | F (g/L · h) |
|---|---|---|---|---|---|
| 1:4 | 60.1 | 25.8 | 0.04 | 0.38 | 0.97 |
| 1:2 | 120.1 | 38.9 | 0.09 | 0.32 | 1.10 |

Where:
A = solid:liquid ratio
B = 100% fermentable sugars produced and not consumed
C = final concentration of ethanol
D = yield of fermentable sugar consumed expressed in terms of biomass
E = yield of fermentable sugar consumed expressed in terms of ethanol
F = rate of production of mass for volume At the end of the fermentation process, which took about 36 hours, at laboratory scale, using a solid:liquid ratio of 1:2, it was possible to obtain 100 L of alcohol in the fermentation medium per tonne of bagasse hydrolysate.

In order to carry out the process of hydrolysis and extraction of the liquid phase from the liquid/solid mixture, a laboratory-scale reactor and press system with a capacity of 3.5 L was designed and built, in stainless steel, in order to prevent contamination of the hydrolysate with metals during heat treatment.

The reactor comprises a cylindrical body the height of which is similar to the diameter thereof, with a close-coupled valve in the lower part of the cylindrical body, in order to enable withdrawal of the hydrolysed material.

The reactor is also provided with a filtration system, which can be coupled internally with the same, consisting of two screens and a stainless steel mesh, in order to separate the solid and liquid phases.

In addition, two covers, which can be adjusted to the reactor by means of screws, enable the device to be used both for hydrolysis and for phase separation. The first cover is used during the hydrolysis process and consists of a steel sheet. The second cover is employed in the step of solids separation, and operates coupled to the hydraulic system of the press, in conjunction with a piston, which acts as a pressing mechanism.

By this means, practically all of the hydrolysed material is separated and recovered for the subsequent fermentation step The principal advantages of using *Pichia stipitis* yeast which has been acclimatized and adapted have been a high alcohol production rate and a decrease in fermentation time. The literature cites fermentation times of the order of 75 hours; but with the process of the invention, fermentation gives results in 25 to 40 hours.

The invention claimed is:

1. A process for producing ethanol from a hydrolysate of a hemicellulose fraction of sugarcane bagasse, said process comprising the steps of:

a) homogenizing sugarcane bagasse together with sulphuric acid;

b) hydrolyzing the homogenized material in a press reactor, wherein said press reactor comprises a piston as a pressing mechanism;

c) extracting the hydrolysate from the press reactor using said pressing mechanism;

d) neutralizing the hydrolysate with calcium hydroxide;

e) filtering the hydrolysate; and f) fermenting the hydrolysate with an acclimatized *Pichia stipitis* biomass, in the presence of stirring and aeration.

2. The process according to claim 1, wherein the homogenization in step (a) has a solid: liquid ratio of between 1:4 to 1:2.

3. The process according to claim 1, wherein the duration of hydrolysis in step (b) is between 30 to 50 minutes.

4. The process according to claim 1, wherein the fermentation occurs for 25 to 40 hours.

5. The process according to claim 1, wherein the ethanol production rate is 0.97 to 1.10 g/L.h.

6. The process according to claim 1, wherein the sulphuric acid has a concentration of 2% or less.

7. The process according to claim 1, wherein the hydrolysis in step (b) is conducted at a pressure of less than 2 atmospheres.

8. The process according to claim 7, wherein the pressure corresponds to a temperature of 110-130° C.

9. The process according to claim 1, wherein the duration of the hydrolysis in step (b) is adjusted based on the solid: liquid ratio of the homogenization in step (a).

* * * * *